US00PP31870P2

(12) United States Plant Patent
Osiecki

(10) Patent No.: US PP31,870 P2
(45) Date of Patent: Jun. 16, 2020

(54) ***MANDEVILLA* PLANT NAMED 'MOGI ONE'**

(50) Latin Name: *Mandevilla hybrida*
Varietal Denomination: MOGI ONE

(71) Applicant: Oglesby Plants International, Inc., Altha, FL (US)

(72) Inventor: Marian Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 0 days.

(21) Appl. No.: 16/602,009

(22) Filed: Jul. 18, 2019

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Mandevilla* cultivar named 'MOGI ONE' is disclosed, characterized by short internodes, deep red flowers, glossy foliage, and rapid growth. Flowering begins early. Plants are vigorous and flower abundantly. The new variety is a *Mandevilla*, typically produced as an indoor ornamental plant.

2 Drawing Sheets

Figure 1:
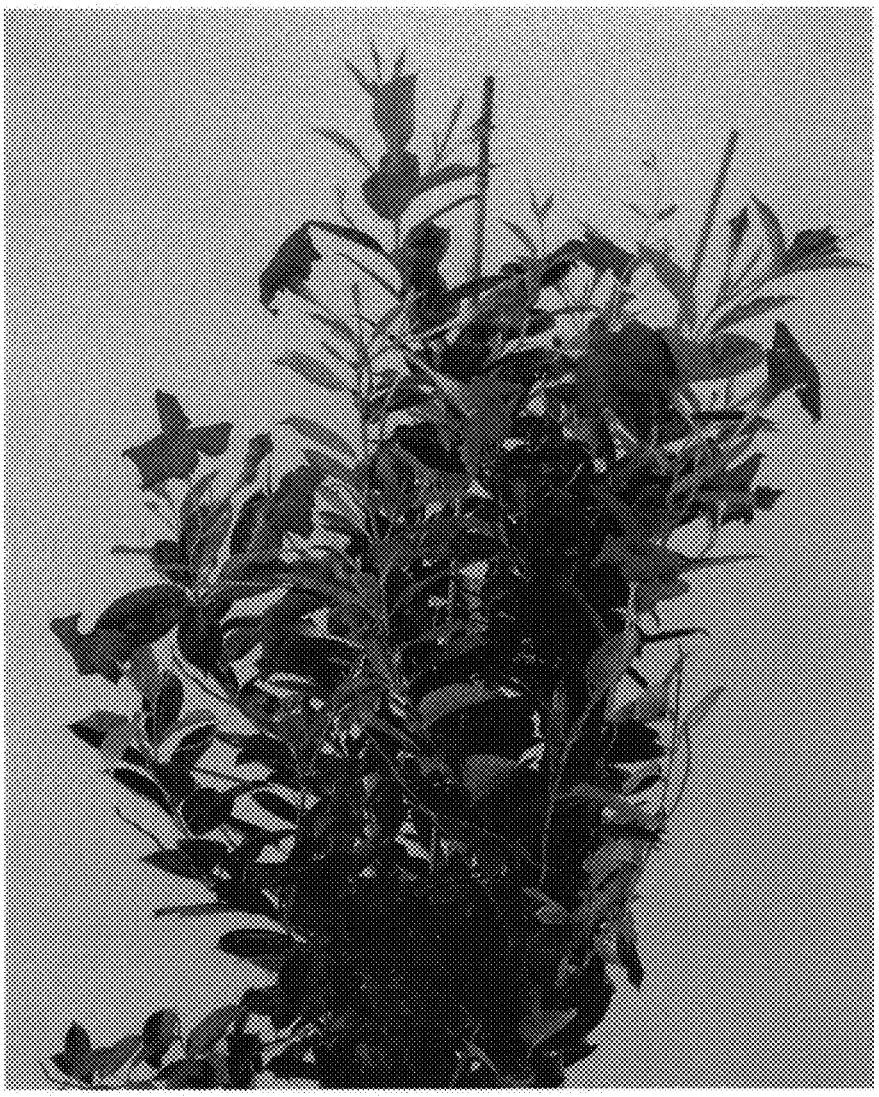

Latin name of the genus and species: *Mandevilla hybrida*.
Variety denomination: 'MOGI ONE'.

BACKGROUND OF THE INVENTION

The new cultivar is a product of a planned breeding program. The objective of the breeding program was to develop new *Mandevilla* varieties with vigorous plant habits suitable for commercial production. The new variety originated from a cross pollination of an unnamed proprietary, unpatented seed parent and the pollen parent, a different, unnamed proprietary, unpatented *Mandevilla*. The crossing was made during March 2013.

The new variety was discovered by the inventor, Marian Osiecki in the Summer of 2014 in a group of seedlings resulting from the crossing. The new cultivar was found in a commercial greenhouse in Altha, Fla.

Asexual reproduction of the new cultivar 'MOGI ONE' was first performed at a commercial nursery in Altha, Fla. by terminal vegetative cuttings in August 2014. Subsequent propagation by tissue culture has shown that the unique features of this cultivar are stable and reproduced true to type in successive generations.

SUMMARY OF THE INVENTION

The cultivar 'MOGI ONE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MOGI ONE'. These characteristics in combination distinguish 'MOGI ONE' as a new and distinct *Mandevilla* cultivar:

1. Deep red flowers.
2. Vigorous plants.
3. Rapid growth.
4. Short internodes.
5. Abundant flowering.

6. Early flowering.
7. Suitable for trellis production or hanging baskets.

PARENT COMPARISON

Plants of the new cultivar 'MOGI ONE' are similar to the seed parent in most horticultural characteristics. The new variety, however, differs in the following:

1. The new variety begins flowering earlier than the seed parent.
2. 'MOGI ONE' produces flowers that are a different shade of red than the seed parent.
3. 'MOGI ONE' glossier foliage than the seed parent.

Plants of the new cultivar 'MOGI ONE' are similar to the pollen parent in most horticultural characteristics. Plants of the new variety however differ in the following:

1. 'MOGI ONE' produces is more vigorous than the pollen parent.
2. 'MOGI ONE' produces red flowers, the pollen parent produces pink flowers.
3. 'MOGI ONE' produces more branches than the pollen parent.

COMMERCIAL COMPARISON

'MOGI ONE' can be compared to the commercial variety *Mandevilla* 'Sunmandecrim' U.S. Plant Pat. No. 15,539 Plants of 'Sunmandecrim' are similar to plants of 'MOGI ONE' in most horticultural characteristics, however, plants of 'MOGI ONE' differ in the following:

1. The new variety has flowers of a more true red color, whereas this comparator produces flowers with more burgundy tones.
2. 'MOGI ONE' begins flowering earlier than this comparator.
3. 'MOGI ONE' produces more flowers than this comparator.

'MOGI ONE' can also be compared to the commercial variety *Mandevilla* 'Sunmandecrikin' U.S. Plant Pat. No. 17,736 Plants of 'Sunmandecrimkin' are similar to plants of 'MOGI ONE' in most horticultural characteristics, however, plants of 'MOGI ONE' differ in the following:

1. The new variety produces flowers that are smaller in diameter than this comparator.
2. 'MOGI ONE' begins flowering earlier than this comparator.
3. 'MOGI ONE' produces more flowers than this comparator.

BRIEF DESCRIPTION OF THE PHOTOGRAPHS

The accompanying photograph in FIG. 1 illustrates in full color a typical plant of 'MOGI ONE' grown in a greenhouse in Altha, Fla. This plant is approximately 14 months old, shown in an 8 inch pot.

Figure 2:
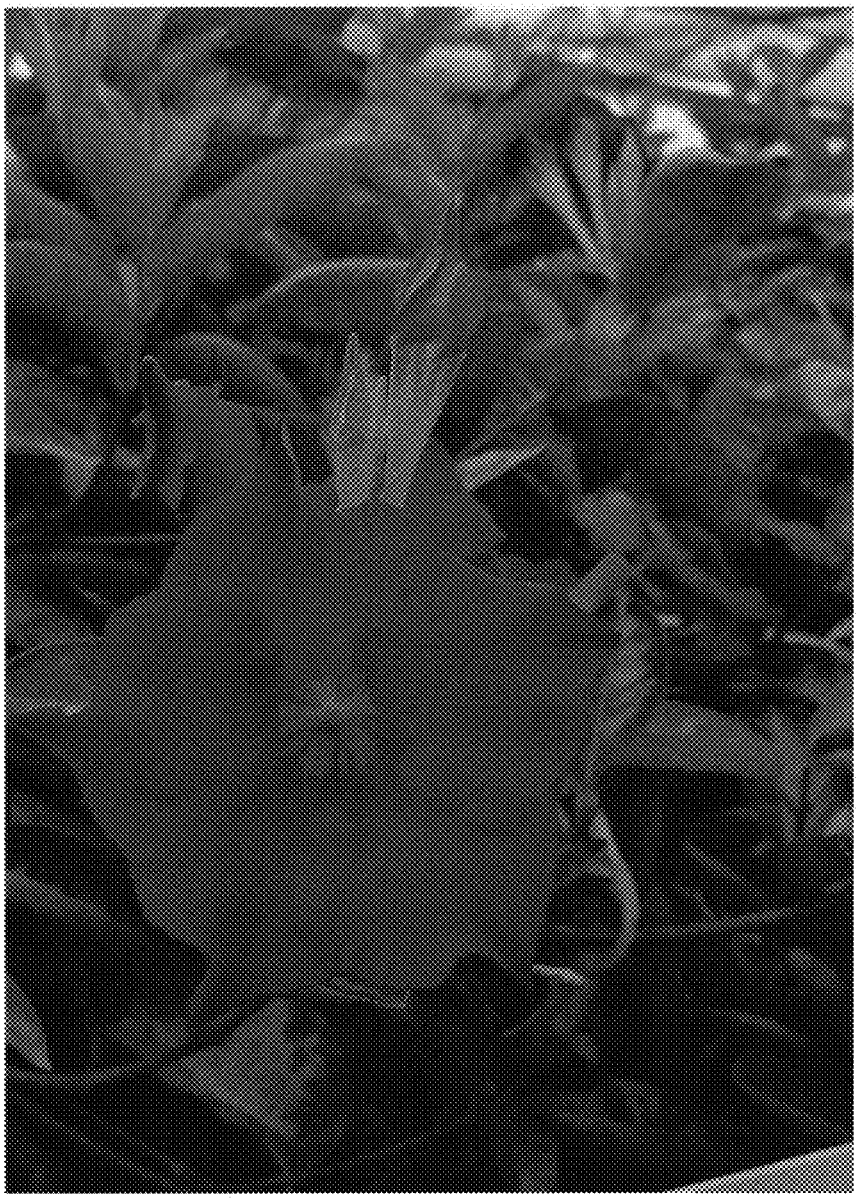

FIG. 2 illustrates a close up view of the flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'MOGI ONE' plants grown in a climate controlled greenhouse in Altha, Fla., USA. Temperatures ranged from 20° C. to 25° C. at night to 25° C. to 32° C. during the day. No artificial light, photoperiodic treatments were given to the plants. Measurements and numerical values represent averages of typical plant types.

Botanical classification: *Mandevilla hybrida* 'MOGI ONE'.

PROPAGATION

Time to initiate roots: About 15 days at approximately 30° C. in the summer. About 25 days at 18° C. in the winter.

Time to produce a rooted cutting: About 50 days at 20 to 30° C.

Root description: Freely branching and white-brown in color. Not accurately measured with R.H.S. chart.

PLANT

Growth habit: Vining evergreen flowering plant. Initially upright, then vining, requiring support to maintain upright habit. Typically, plants are pinched approximately 3 months after planting a rooted cutting to encourage branching.

Age of plant described: 10 months.

Container size: 5 gallon.

Height: Approximately 134 cm.

Plant spread: Approximately 76 cm.

Growth rate: Moderate.

Branching characteristics: Strong branching occurs after pinch.

Length of primary lateral branches: Approximately 31 cm.

Diameter of lateral branches: Approximately 0.4 cm.

Lateral branch color: Near RHS Greyed-Orange 177B.

Internode length: Approximately 8 cm.

Stem texture: Glabrous.

FOLIAGE

Leaf:

*Arrangement*.—Opposite, simple.

*Average length*.—Approximately 8.4 cm.

*Average width*.—Approximately 5.5 cm.

*Shape of blade*.—Elliptic.

*Apex*.—Acute to Cuspidate.

*Base*.—Cordate to Obtuse.

*Attachment*.—Petiolate.

*Margin*.—Entire.

*Texture of top surface*.—Glabrous. Shiny.

*Texture of bottom surface*.—Glabrous. Matte.

*Leaf internode length*.—Approximately 4.1 cm.

*Color*.—Young foliage upper side: Near RHS Green 137A. Young foliage under side: Near RHS Green 138B. Mature foliage upper side: Near RHS Green 137A. Mature foliage under side: Near RHS Green 138B.

*Venation*.—Type: Pinnate. Venation color upper side: Near RHS Yellow-Green 144A. Venation color under side: Near RHS Yellow-Green 139C.

*Petiole*.—Average Length: Approximately 1.0 cm. Color: Near RHS Yellow-Green 144A. Diameter: Approximately 0.23 cm. Texture: Glabrous.

FLOWER

Natural flowering season: Naturally flowers Summer through late Autumn.

Inflorescence type and habit: Single salverform flower; terminal or axillary; flowers face outward and upward.

Rate of flower opening: Approximately 6 days from bud to fully opened flower.

Flower longevity on plant: 4 to 5 days, after fully opened. Self-cleaning.

Quantity of flowers: Free flowering, young plants have at least 20 flowers at all times; approximately 50 to 100 flowers on older plants.

Inflorescence size:

*Diameter*.—Approximately 8.5 cm.

*Length*.—Approximately 7.4 cm.

*Corolla tube length*.—Approximately 5.0 cm.

*Corolla tube diameter*.—Average 9 mm.

*Corolla tube texture*.—Glabrous.

*Throat diameter*.—Approximately 1.1 cm.

Corolla:

*Petal arrangement*.—Single whorl of 5 imbricate petals, fused into flared trumpet.

*Size*.—Lobe Length: 3.5 cm. Lobe Width: 3.4 cm.

*Margin*.—Entire.

*Apex*.—Rounded shallow lobe with acute apex.

*Texture*.—Smooth, velvety.

Color:

*Petals*.—When opening: Upper surface: Near RHS Red 46A. Lower surface: Near RHS Red 47B. Fully opened: Upper surface: Near RHS Red 46A and 46B, both colors present individually. Lower surface: Near RHS Red 47A and 47B both colors present individually. Tube color (interior): Near RHS Orange N25A with streaks near RHS Red 46B. Tube color (exterior): Near RHS Green-White 157A with streaks near RHS Red 47B. Throat color: Near RHS Red 46B, striped Yellow 13A. Color Changes when Aging: Red 46A flushed Orange-Red N34A.

Bud:

*Shape*.—Ovate to Lanceolate.

*Length*.—Approximately 7.3 cm.

*Diameter*.—Approximately 1.6 cm.

*Color*.—Near RHS Yellow-Green 145C at base; near RHS Green-White 157A with streaks near RHS Red 47B in middle; near RHS Red 47B at apex.

Sepals:

*Arrangement.*—5 per flower in a single whorl; fused.
*Shape.*—Narrowly deltoid.
*Quantity.*—5.
*Length.*—Approximately 0.8 cm.
*Width.*—Approximately 0.2 cm.
*Margin.*—Entire.
*Apex.*—Acuminate.
*Texture.*—Smooth, waxy.
*Color.*—Upper surface: Near RHS Yellow-Green 145C. Lower surface: Near RHS Yellow-Green 145C.

Peduncles:

*Length.*—Approximately 1.8 cm.
*Width.*—Approximately 0.25 cm.
*Angle.*—Almost straight, slight undulation or curve.
*Strength.*—Flexible and strong.
*Color.*—Near RHS Yellow-Green 145C.
*Texture.*—Glabrous.

Fragrance: None.

REPRODUCTIVE ORGANS

Stamens:

*Number.*—5, anthers fused together at tips, filaments fused to corolla.
*Anther length.*—0.8 cm.
*Anther color.*—Near RHS Yellow 4D.
*Anther shape.*—Oblong.
*Pollen.*—None observed.

Pistil:

*Number.*—1.
*Length.*—Approximately 2.7 cm.
*Style color.*—Near RHS White 155D.
*Stigma.*—Shape: Globular. Color: Near RHS Greyed-Green 193B. Ovary color: Near RHS Green 138B.

OTHER CHARACTERISTICS

Disease resistance: Improved resistance to normal diseases of *Mandevilla* have been observed.

Drought tolerance and cold tolerance: Tolerates temperatures from approximately 0° C. to 40° C. and does not tolerate drought.

Fruit/seed production: Not observed.

What is claimed is:

1. A new and distinct cultivar of *Mandevilla* plant named 'MOGI ONE' as herein illustrated and described.

* * * * *